US006161095A

United States Patent [19]
Brown

[11] Patent Number: 6,161,095
[45] Date of Patent: *Dec. 12, 2000

[54] TREATMENT REGIMEN COMPLIANCE AND EFFICACY WITH FEEDBACK

[75] Inventor: Stephen J. Brown, Woodside, Calif.

[73] Assignee: Health Hero Network, Inc., Mountain View, Calif.

[*] Notice: This patent is subject to a terminal disclaimer.

[21] Appl. No.: 09/216,012

[22] Filed: Dec. 16, 1998

[51] Int. Cl.[7] .................................................. G06F 17/60
[52] U.S. Cl. ........................................ 705/2; 705/3
[58] Field of Search .......................... 705/2, 3; 600/300

[56] References Cited

U.S. PATENT DOCUMENTS

| | | | |
|---|---|---|---|
| 5,642,731 | 7/1997 | Kehr ........................................ | 600/300 |
| 5,675,635 | 10/1997 | Vos et al. . | |
| 5,752,235 | 5/1998 | Kehr et al. ................................. | 705/3 |
| 5,796,393 | 8/1998 | MacNaughton et al. . | |
| 5,800,458 | 9/1998 | Wingrove .................................. | 607/2 |
| 5,832,448 | 11/1998 | Brown ....................................... | 705/2 |
| 5,835,896 | 11/1998 | Fisher et al. . | |
| 5,875,432 | 2/1999 | Sehr . | |
| 5,899,855 | 5/1999 | Brown ....................................... | 600/301 |
| 5,945,651 | 8/1999 | Chorosinski et al. .................... | 235/375 |
| 5,954,641 | 9/1999 | Kehr et al. ............................... | 600/300 |
| 5,960,403 | 9/1999 | Brown ........................................ | 705/2 |

FOREIGN PATENT DOCUMENTS

WO 95/22131   8/1995   WIPO .......................... G08B 25/10

OTHER PUBLICATIONS

Wilkins, Aaron. "Expanding Internet access for health care consumers", Health Care Management Review, Summer, Jul. 1999, 24–30.

"Towards a partnership of care", M2 Presswire, Jun. 14, 2000.

*Primary Examiner*—James P. Trammell
*Assistant Examiner*—Chang Y. Chung
*Attorney, Agent, or Firm*—Black Lowe & Graham PLLC

[57] ABSTRACT

A method and system for interaction with a community of individuals, relating to compliance with a treatment regimen. Individuals interact with a protocol or intelligent message to provide assistance in all aspects of treatment regimen compliance, data collection, supply, review and modification.

10 Claims, 3 Drawing Sheets

TREATMENT REGIMEN COMPLIANCE AND EFFICACY WITH FEEDBACK

RELATED APPLICATIONS

Inventions described herein can be used in combination or conjunction with inventions described in the following patent application(s):

application Ser. No. 09/210,323, Express Mail Mailing No. EE143637591US, filed Nov. 30, 1998, in the name of Stephen J. Brown, titled "Leveraging Interaction with A Community of Individuals," assigned to the same assignee, and all pending cases claiming priority thereof.

These applications are each hereby incorporated by reference as if fully set forth herein. These applications are collectively referred to herein as "incorporated disclosures."

BACKGROUND OF THE INVENTION

1. Field of the Invention

This invention relates to interaction with a community of individuals, relating to treatment regimen compliance and efficacy, including supply and use of pharmaceuticals.

2. Related Art

When medical personnel prescribe treatment regimens for patients or "patients" undertake non-prescription treatment regimens (whether such regimens are prescribed or undertaken for medication, physical therapy, psychological therapy, self-improvement, or other purposes), a problem can arise in assuring that the patients comply with the requirements of the treatment regimen. For example, some patients are disorganized, forgetful, or simply unwilling to comply. When the treatment regimen has potential side effects, or when the treatment regimen is to be followed under stated conditions (for example: taking medicine with meals, not with alcohol, or in the evening), patient compliance can be relatively reduced even further. When the treatment regimen is relatively complex, some patients are even unable or unwilling to manage that treatment regimen.

Known methods for monitoring and controlling treatment regimens are relatively costly and limited in capability. Some known methods are described in the following patents:

U.S. Pat. No. 5,408,443, "Programmable Medication Dispensing System," issued Apr. 18, 1995 in the name of Edward D. Weinberger.

U.S. Pat. No. 5,642,731, "Method of and Apparatus for Monitoring the Management of Disease," issued Jul. 1, 1997 in the name of Bruce A. Kehr.

U.S. Pat. No. 5,752,235, "Electronic Medication Monitoring and Dispensing Method," issued May 12, 1998 in the name of Bruce A. Kehr, et al.

While these known methods generally achieve the goal of monitoring and controlling a treatment regimen, particularly a medication regimen, they suffer from several drawbacks and limitations.

First, there is a need to provide a portable system to monitor and encourage compliance, and facilitate data collection, so that patients are restricted as little as possible regarding their activities and movements.

Second, there is a need to determine if patients are actually complying with treatment regimens at times when the patients are relatively remote to client devices for the system. Known methods do not provide adequate feedback to determine whether patients are complying with the treatment regimen unless they remain relatively local to client devices.

Third, there is a need to determine whether treatment regimens have the desired and intended effects. Known methods do not provide adequate feedback to determine whether treatment regimens are effective, or whether patients are suffering any untoward side effects. Using known methods, medical personnel must generally wait for patients to complain, or for medical tests to show, that prescribed treatment regimens are inadequate or are producing side effects. Similarly, using known methods, patients undertaking non-prescribed treatment regimens generally do not have effective or convenient systems to monitor and record whether non-prescribed treatment regimens are producing intended results.

Fourth, there is a need to inform patients to follow treatment regimens, particularly when patients are forgetful or treatment regimens are complex. Although known methods do include reminders to patients, it would be advantageous to tailor those reminders to patients' actual compliance history (thus, providing fewer reminders when they are relatively less necessary and more reminders when they are relatively more necessary).

Fifth, there is a need to leverage expert knowledge to improve response to feedback from patients, and to reduce the time and expense required for' medical personnel to individually monitor, evaluate and modify treatment regimens.

Sixth, there is a need to broaden application of reminder and expert knowledge leveraging systems beyond medication regimens, to include physical, psychological, self-improvement and other treatment regimens.

Accordingly, it would be advantageous to provide a portable device that can be coupled and uncoupled to a communication system with feedback to monitor patient compliance with, and effectiveness of, treatment regimens, so that input from patients regarding treatment regimens can be recorded, reviewed, analyzed and otherwise generally acted upon. Medical personnel and/or patients can thus (1) monitor compliance with treatment regimens, (2) monitor effectiveness or side effects of treatment regimens, (3) remind patients no more than necessary, and (4) possibly alter treatment regimens in response to feedback from patients. These advantages are achieved in embodiments of the invention in which a portable device is intermittently coupled to a client device in a client-server system, the patient enters information to the portable device about following the treatment regimen while the portable device is uncoupled, and medical personnel or the patient can receive that information and possibly alter the behavior of the portable device when the portable device is re-coupled to the system.

SUMMARY OF THE INVENTION

The invention provides a method and system for interaction with a community of individuals, relating to compliance with and effectiveness of treatment regimens, including supply and use of pharmaceuticals, using a protocol or other intelligent message which acts in place of a service provider and which is capable of collecting or imparting information to patients in place thereof. Individuals interact with the protocol or intelligent message to provide assistance in all aspects of treatment regimen compliance, data collection, supply or delivery, review and modification. These aspects can include (1) reminders regarding compliance with a selected treatment regimen for medication, physical therapy, psychological therapy, self-improvement, or some combination thereof, (2) data collection of facts regarding patient compliance, symptomology, possible drug interactions or side effects of medication if required by the treatment regimen, and other facts relevant to evaluation and possible modification of the treatment regimen; (3) networked integration with workstations for medical professionals to automate approvals and modifications, and refills and delivery of medication if required by the treatment regimen.

A system includes a set of client devices and a server device. A service provider determines a treatment regimen for selected patients, determines a protocol to be followed by the client devices to assist the patient in complying with that treatment regimen [in assisting with that medication regimen] and to maximize effectiveness of treatment, and sends that protocol to the server device. The server device can update (responsive to the protocol) selected instructions at the client devices, and can receive (responsive to selected instructions) information from the client devices regarding their associated patients.

In a first preferred embodiment, a client device, located locally to a patient, couples to a portable device (such as a cellular telephone, pager, "Palm Pilot" or other handheld computer, or watch), capable of being carried away by the patient to locations relatively remote from the client device. The client device can interact with the portable device: (1) to provide the portable device with the capability of reminding the patient regarding the treatment regimen, or (2) to provide the portable device with the capability of further data collection regarding the patient. The client device can interact with the portable device using a docking connection, an infrared connection, a radio-frequency connection, a plug-in connection, or another suitable connection.

DETAILED DESCRIPTION OF THE PREFERRED EMBODIMENT

In the following description, a preferred embodiment of the invention is described with regard to preferred process steps and data structures. Embodiments of the invention can be implemented using general purpose processors or special purpose processors operating under program control, or other circuits, adapted to particular process steps and data structures described herein. Implementation of the process steps and data structures described herein would not require undue experimentation or further invention.

System Elements

Figure 1:
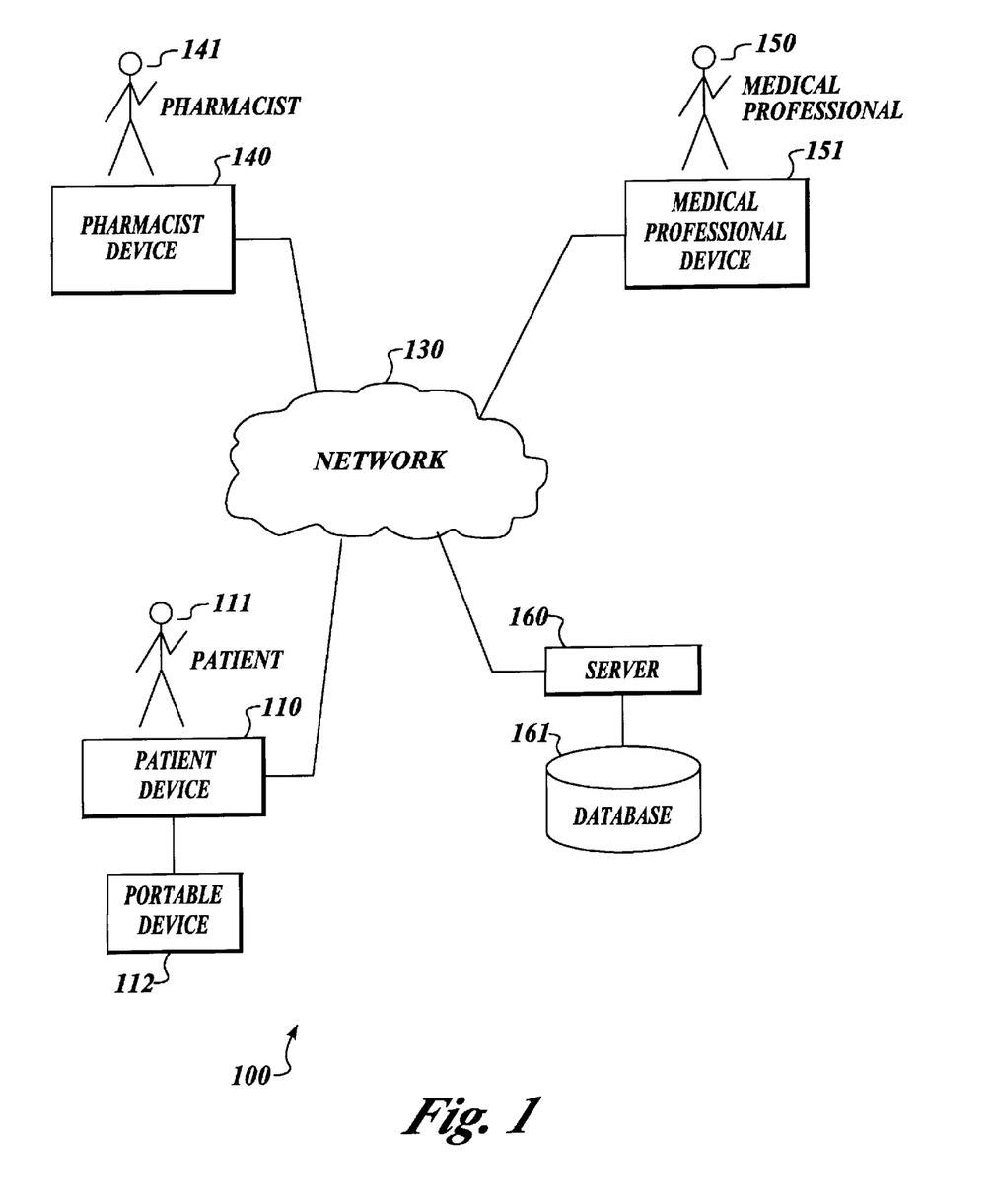
FIG. 1 shows a block diagram of a system for interaction with a community of individuals to encourage and monitor compliance with a treatment regimen, using a protocol or other intelligent message which acts in place of a service provider to collect and impart information relevant to the treatment regimen.

FIG. 1 shows a block diagram of a system 100 to encourage and monitor compliance with a treatment regimen using a protocol or other intelligent message which acts in place of a service provider to collect and impart information relevant to the treatment regimen, including a patient device 110, a pharmacist device 140, a medical professional device 150, and a server device 160, said devices being coupled using a communication network 130, and a portable device 112 which can be coupled to the patient device 110 to receive information regarding the treatment regimen and send feedback from the patient 111 responsive thereto.

For further information regarding a data structure and simplified patient interaction interface, and preferred embodiments of the patient device 110, pharmacist device 140, medical professional device 150, and the server device 160 including database 161 of treatment regimen information, see related application Ser. No. 09/210,323, Express Mail Mailing No. EE143637591US, filed Nov. 30, 1998, in the name of Stephen J. Brown, titled "Leveraging Interaction with A Community of Individuals," assigned to the same assignee, attorney docket number HHN-007, and other related applications incorporated by reference therein.

For further information regarding the protocol or other intelligent message used by the system, see related application Ser. No. 09/203,882, Express Mail Mailing No. EE143637565US, filed Dec. 1, 1998, in the name of Stephen J. Brown, titled "Remote User Data Collection Protocols Including Data Structures and User Interface," assigned to the same assignee, attorney docket number HHN-002, and other related applications incorporated by reference therein.

For further information regarding a medicine dispenser which can be used by the system, see related application Ser. No. 09/203,880, Express Mail Mailing No. EE143637557US, filed Dec. 1, 1998, in the name of Stephen J. Brown, et al., titled "Using A Computer Communication System With Feedback to Dispense Medicine," assigned to the same assignee, attorney docket number HHN-005, and other related applications incorporated by reference therein.

Portable Device

Figure 3:
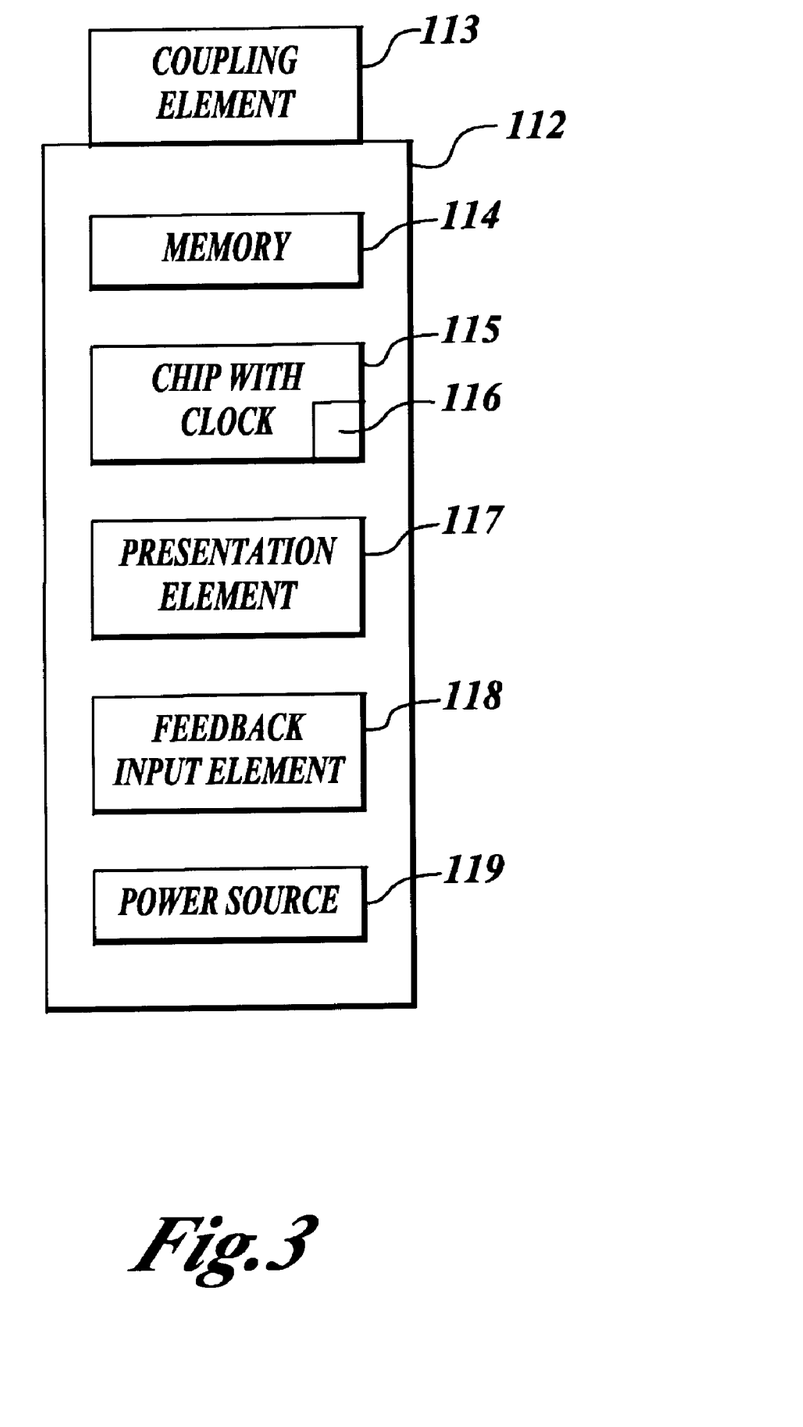
FIG. 3 shows a first preferred embodiment of a portable device used by the system to encourage and monitor compliance with a treatment regimen, and to collect and impart information relevant to the treatment regimen.

FIG. 3 shows a first preferred embodiment of a portable device 112 used by the system 100.

In a first preferred embodiment, the portable device 112 includes a coupling element 113 for coupling the portable device 112 to the patient device 110, a memory element 114, a processor chip 115 including a clock circuit 116, a presentation element 117, and a patient feedback input element 118.

A service provider determines a treatment regimen for selected patients 111 and a protocol to be followed by their portable devices 112 to assist the patients 111 in following the treatment regimen. The service provider sends the treatment regimen and protocol to the server device 160 where it is recorded in the database 161. The server device 160 sends the treatment regimen and protocol information to the patient device 110, and optionally to the pharmacist device 140 and the medical professional device 150.

The portable device 112 is coupled to the patient device 1 10 using the coupling element 113. The coupling element 113 may couple using a docking station, an infrared connection, a radio-frequency connection, a plug-in connection, other suitable means or any variant thereof While coupled, the treatment regimen and protocol information received by the patient device 110 is sent to the portable device 112 and recorded in the memory 114. In a first preferred embodiment, the power source 119 is rechargeable and the charge can be replenished by the patient device 110 while the portable device 112 is coupled to it. In alternative embodiments, the power source 119 is rechargeable and the charge can be replenished by some other device, or includes one or more disposable batteries.

After the treatment regimen and protocol information is recorded in the memory 114, the portable device 112 can be uncoupled from the patient device 110 and taken with the patient 110 to locations relatively or logically remote from the patient device 110. Whether the portable device 112 coupled or uncoupled to the patient device 110, when the patient 111 is due to perform an act according to the treatment regimen, the portable device 112 uses the presentation element 117 to provide a reminder message instructing the patient 111 to perform that act. In a first preferred embodiment, the act to be performed is related to compliance with a medication regimen including, without limitation, obtaining medicine, taking medicine, taking medicine with another substance such as food or water, not taking medicine with another substance such as alcohol or incompatible medications, or obtaining a prescription refill. In alternative embodiments, the act to be performed may be pursuant to a physical therapy regimen including, without limitation, exercising, stretching, changing position, or changing work routine; pursuant to a psychological therapy regimen including, without limitation, repeating an affirmation, meditation, self-hypnosis or other mental activity; or pursuant to a self-help regimen or other type of treatment regimen such as weight loss including, without limitation, drinking water or eating a snack.

The patient 111 performs the indicated act and enters a message into the portable device 112 confirming performance of the act using the patient feedback input element 118. Operation of the patient feedback input element 118 causes the processor chip 115 to cancel the reminder message, check the clock 116, and record the time and fact of performance in the memory 114. In a first preferred embodiment, the patient 111 also enters additional information relevant to monitoring and evaluating the treatment regimen in response to queries by the presentation element 117 in accordance with the treatment regimen and protocol.

The number of reminder messages provided to the patient 111, and the number of messages from the patient 111 confirming performance of the indicated acts and/or providing other information relevant to compliance with and effectiveness of the treatment regimen, is limited only by the memory capacity of the portable device 112.

In a first preferred embodiment, the presentation element 117 is a human-readable visual display using LCD's, LED's, or other suitable devices. In alternative preferred embodiments, the presentation element 117 can be a device which produces human-intelligible sound, or a combination of devices which produce human-intelligible visual and audible signals.

At some later time, the portable device 112 is re-coupled to the patient device 110 using the coupling element 113, causing the contents of the memory 114 to be downloaded into the patient device 110 and sent to the server device 160 for recording in the database 161. Such a time may be as is convenient to the patient 111, or according to a selected maximum time interval dictated by the treatment regimen and protocol, or as is required to replenish the power source 119 of the portable device 112, or in accordance with other requirements of the system 100.

At the server device 160, the protocol or other intelligent message reviews and compares the information provided by the patient 111 to the requirements of the treatment regimen in order to evaluate the effectiveness of the treatment regimen towards achieving treatment objectives and as to compliance of the patient 111 with the treatment regimen. The protocol may then leave the treatment regimen unchanged or modify it as needed to increase effectiveness and/or compliance; in either case, the server device 160 sends a message to the patient device 110 as to the regimen to be followed from that time forward. In a preferred embodiment, the server device 160 also sends that message to the pharmacist device 140 and the medical professional device 150. For additional information regarding the protocol used by the system 100 and interaction of the protocol with other elements of the system 100, see discussion above at System Elements regarding related applications.

In a first preferred embodiment, information regarding the entire course of the treatment regimen, such as each updated regimen and its effectiveness and relative compliance by the patient can be stored by each of those devices and displayed on demand. In alternative embodiments, only the server records the entire course, or only selected devices, or some combination thereof.

In a preferred embodiment, when a treatment regimen requires a patient 111 to take one or more medications, the portable device 112 can be coupled to a medication dispenser containing medication specified by the treatment regimen. In an alternative embodiment, the portable device 112 also controls the medication dispenser so as to release only the correct dosage of the correct medication at the correct time responsive to the treatment regimen. In a further alternative preferred embodiment, the dispenser automatically provides feedback to the portable device 112 when the correct medication is removed, canceling the reminder message and storing the feedback for subsequent downloading to the patient device 110 on the next occasion that the portable device 112 is coupled to the patient device 110.

The patient device 110 can be any device for electronic communication including, but not limited to, an application specific device, a hard-wired telephone, a cellular telephone, a pager, a personal desktop computer, a personal notebook computer, a hand-held computing device, an internet appliance, an internet-enabled television such as WebTV, personal digital assistant such as the Palm III, or any variant thereof.

The portable device 112 can be any portable device for electronic communication which is capable of being coupled to the patient device 110 including, without limitation, an application specific device, a cellular telephone, a pager, a personal notebook computer, a hand-held computing device, an internet appliance, a personal digital assistant such as the Palm III, a watch, or any variant thereof.

The feedback input element 118 can be any means of providing input to an electronic communication device including, but not limited to, a button, a telephone key, a computer keyboard key, a voice-response activator, or any variant or combination thereof.

Method of Operation

Figure 2:
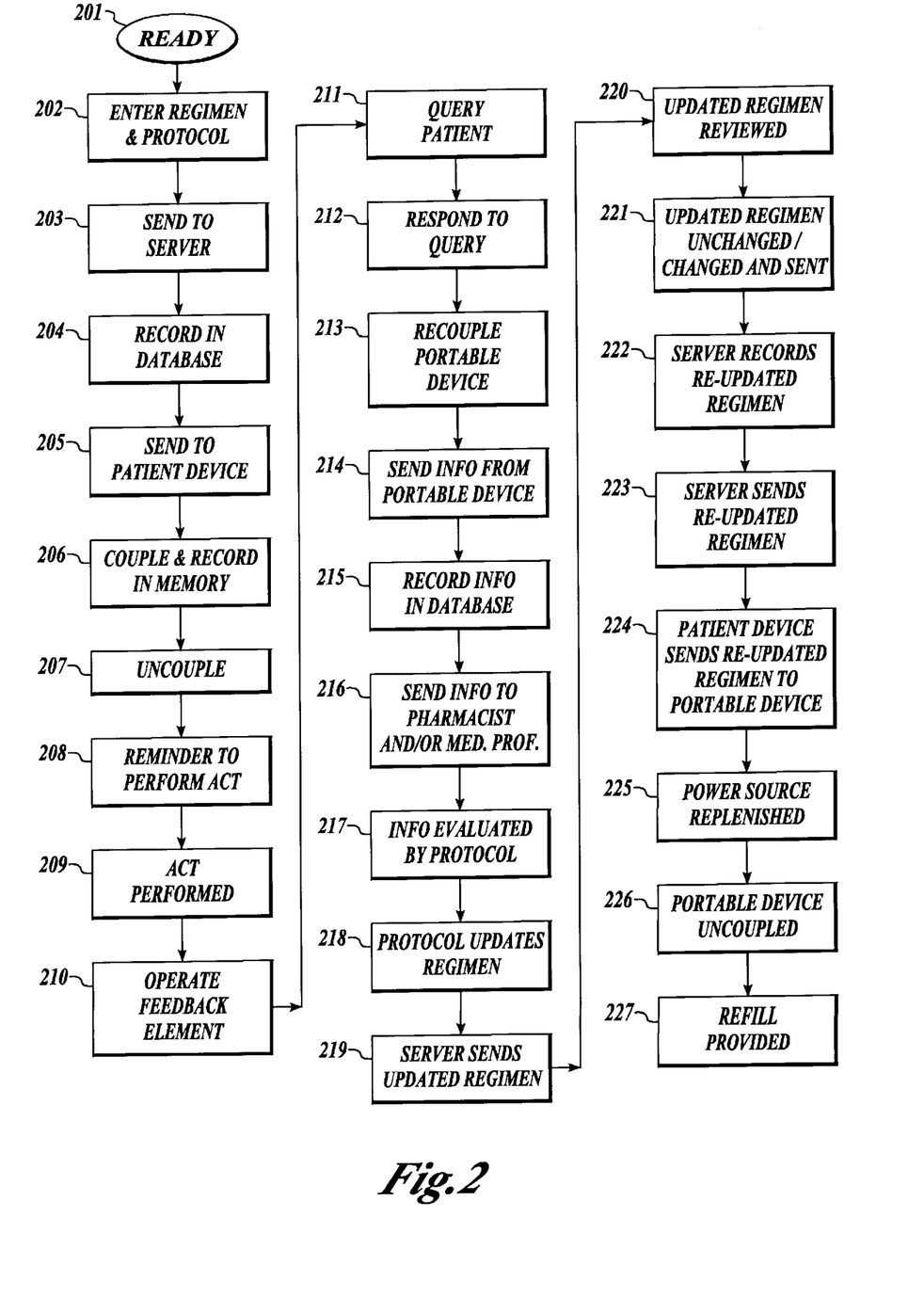
FIG. 2 shows a process flow diagram of a method for operating a system for interaction with a community of individuals to encourage and monitor compliance with a treatment regimen, using a protocol or other intelligent message which acts in place of a service provider to collect and impart information relevant to the treatment regimen.

FIG. 2 shows a process flow diagram of a method for operating a system for leveraging expert interaction with a community of individuals to encourage compliance with a treatment regimen and for collecting and imparting information relevant to that treatment regimen.

A method 200 is performed by the system 100, as follows:

At a flow point 201, the system 100 is ready to proceed.

At a step 202, a service provider enters information concerning a treatment regimen and protocol to be followed by the patient 111.

At a step 203, the treatment regimen and protocol information is sent to the server device 160 using the communications network 130.

At a step 204, the server device 160 records the treatment regimen and protocol information received from the service provider in the database 161.

At a step 205 in a preferred embodiment, the server device 160 sends the treatment regimen and protocol information to the patient device 110, the pharmacist device 140 and the medical professional device 150 using the communication network 130. In alternative embodiments, the server device 160 may send the treatment regimen and protocol information only to the patient device 110.

At a step 206, the portable device 112 is coupled to the patient device 110 and the treatment regimen and protocol information is copied into the memory 114 of the portable device 112.

At a step 207, the portable device 112 is uncoupled from the patient device 110 and is taken with the patient 111 to a location relatively remote from the patient device 110.

At a step 208, responsive to the treatment regimen and protocol information stored in the memory 114 in conjunction with input from the clock 116, the patient device 110 uses the presentation element 117 to provide a reminder message to the patient 111 that an act is required to be performed by the patient 111 and instructs the patient 111 regarding the act to be performed.

At a step 209, the patient 111 performs the indicated act as directed.

At a step 210, the patient 111 operates the feedback input element 118 on the portable device 112, canceling the reminder message.

At a step 211, the portable device 112 uses the presentation element 117 to query the patient 111 to provide information responsive to the protocol for evaluating the effectiveness of the treatment regimen.

At a step 212, the patient 111 operates the feedback input element 117 to provide information responsive to the queries, and that information is recorded in the memory 114.

At a step 213, the portable device 112 is re-coupled to the patient device 110.

At a step 214, the information stored in the memory 114 is sent to the patient device 110, which in turn sends that information to the server device 160 using the communication network 130.

At a step 215, the information received by the server device 160 is recorded in the database 161.

At a step 216, in a preferred embodiment the server device 160 sends the information received from the patient device 110 to the pharmacist device 140 and to the medical professional device 150 using the communication network 130. In an alternative embodiment, the server device 160 does not send the information received from the patient device 110 to the pharmacist device 140 or to the medical professional device 150, whether using the communication network 130 or otherwise.

At a step 217, the information received by the server device 160 from the patient device 110 is evaluated by the protocol.

At a step 218, the protocol updates the treatment regimen and either leaves it unchanged or modifies it in accordance with the protocol logic.

At a step 219 in a preferred embodiment, the server device 160 sends the updated treatment regimen information to the patient device 110, to the pharmacist device 140 and to the medical professional device 150, using the communication network 130. In an alternative embodiment, the server device 160 does not sent the updated treatment regimen information to the pharmacist device 140 or the medical professional device 150.

At a step 220 in a preferred embodiment, the pharmacist 141 and/or the medical professional 151 review and compare the original treatment regimen, the compliance and other information input by the patient 111, and the updated treatment regimen, and either leave the updated treatment regimen and protocol information unchanged or modify it as necessary. In an alternative embodiment, step 220 does not take place.

At a step 221 in a preferred embodiment, the treatment regimen and protocol information as unchanged or as modified by the pharmacist 141 and/or the medical professional 151 is sent to the server device 160 using the communication network 130. In an alternative embodiment, step 221 does not take place.

At a step 222, the server device 160 records the treatment regimen and protocol information as unchanged or as modified by the pharmacist 141 and/or the medical professional 151 in the database 161. In an alternative embodiment, step 222 does not take place.

At a step 223 in a preferred embodiment, the server device 160 sends the treatment regimen and protocol information as unchanged or as modified by the pharmacist 141 and/or the medical professional 151 to the patient device 110 using the communication network 130. In an alternative embodiment, step 223 does not take place.

At a step 224, the patient device 110 sends the updated treatment regimen information to the portable device 112 and it is recorded in the memory 114.

At a step 225, the patient device 110 replenishes the charge of the power source 119.

At a step 226, the patient 111 uncouples the portable device 112 from the patient device 110.

At a step 227, the pharmacist 141 provides a refill or new medicine to the patient 111 responsive to the treatment regimen and protocol infortmation. In an alternative embodiment, step 227 does not take place.

Alternative Embodiments

Although preferred embodiments are disclosed herein, many variations are possible which remain within the concept, scope, and spirit of the invention, and these variations would become clear to those skilled in the art after perusal of this application.

What is claimed is:

1. A method of encouraging patient compliance with a treatment regimen, said method including steps for providing first information about said treatment regimen to a server device in a client-server system;

sending said first information to a portable proxy device for a client device in said client-server system;

receiving second information from said patient at said portable proxy device regarding compliance with said treatment regimen;

sending said second information from said portable proxy device to said server device; and comparing said first information with said second information.

2. A method as in claim 1, including steps for altering a sequence of processing steps at said portable proxy device in response to said server device.

3. A method as in claim 1, including steps for altering a sequence of processing steps at said portable proxy device in response to a result of said steps for comparing.

4. A method as in claim 1, including steps for controlling a medicine dispenser coupled to said portable proxy device in response to said second information.

5. A method as in claim 1, including steps for presenting a reminder at said portable proxy device regarding following said treatment regimen.

6. A method as in claim 1, including steps for presenting a reminder from said server device regarding compliance with said treatment regimen.

7. A method as in claim 1, including steps for presenting a result of said steps for comparing to an operator at said server device.

8. A method as in claim 1, including steps for receiving third information at said portable proxy device regarding an effect of an act performed responsive to said treatment regimen.

9. A method as in claim 8, where said third information relates to an effect of medicine taken by said patient responsive to said reminder.

10. A method as in claim 8, including steps for altering said first information in response to said third information.

* * * * *

(12) EX PARTE REEXAMINATION CERTIFICATE (7378th)
United States Patent
Brown (10) Number: US 6,161,095 C1
(45) Certificate Issued: *Feb. 23, 2010

(54) TREATMENT REGIMEN COMPLIANCE AND EFFICACY WITH FEEDBACK

(75) Inventor: Stephen J. Brown, Woodside, CA (US)

(73) Assignee: Health Hero Network, Mountain View, CA (US)

Reexamination Request:
No. 90/009,239, Nov. 6, 2008

Reexamination Certificate for:
Patent No.: 6,161,095
Issued: Dec. 12, 2000
Appl. No.: 09/216,012
Filed: Dec. 16, 1998

(*) Notice: This patent is subject to a terminal disclaimer.

(51) Int. Cl.
*G06Q 50/00* (2006.01)

(52) U.S. Cl. ............................................. 705/2; 705/3
(58) Field of Classification Search ....................... None
See application file for complete search history.

(56) References Cited
U.S. PATENT DOCUMENTS

| | | | |
|---|---|---|---|
| 4,803,625 A | | 2/1989 | Fu et al. |
| 5,019,974 A | * | 5/1991 | Beckers ...................... 600/316 |
| 5,307,263 A | | 4/1994 | Brown |
| 5,381,138 A | | 1/1995 | Stair et al. |
| 5,390,238 A | * | 2/1995 | Kirk et al. .............. 379/106.02 |
| 5,521,589 A | | 5/1996 | Mondrosch et al. |
| 5,664,228 A | | 9/1997 | Mital |
| 5,722,418 A | | 3/1998 | Bro |
| 5,827,180 A | | 10/1998 | Goodman |
| 5,950,632 A | | 9/1999 | Reber et al. |

FOREIGN PATENT DOCUMENTS

WO    WO 97/08605    3/1997

OTHER PUBLICATIONS

"Definition of: client/server" from PCMAG.COM, http://www.pcmag.com/encyclopedia_term/0,2542,t=clientserver&i=39801,00.asp <last visited Mar. 20, 2009>.*
"Motorola introduces PCMCIA 28.8 modem/fax/Ethernet LAN adapter with cellular and paging connectivity", Business Wire, Oct. 30, 1995.
R. Brian Haynes "Improving Patient Compliance in the Management of Hypertension" in Individualized therapy of Hypertension pp. 257–273 (Kaplan and Ram, eds., 1995).

* cited by examiner

*Primary Examiner*—Jeanne M Clark (57) ABSTRACT

A method and system for interaction with a community of individuals, relating to compliance with a treatment regimen. Individuals interact with a protocol or intelligent message to provide assistance in all aspects of treatment regimen compliance, data collection, supply, review and modification.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–10 are determined to be patentable as amended.

1. A method of encouraging patient compliance with a treatment regimen, said method including steps for providing first information about said treatment regimen to a server device in a client-server system;
   sending said first information to a client device in said client-server system;
   sending said first information to a portable [proxy] device [for a] *when said portable device is connected to said* client device in said client-server system;
   *storing said first information in a memory of said portable device;*
   presenting instructions or queries to said patient via a presentation element of said portable device regarding compliance with said treatment regimen, *wherein said instructions and queries are (i) based on the first information stored in said memory and (ii) presented in response to a timing signal received from a clock circuit of said portable device;*
   receiving second information from said patient [at] *via a feedback input element of* said portable [proxy] device, *wherein said second information is responsive to said instructions or queries* regarding compliance with said treatment regimen;
   *storing said second information in said memory of said portable device while said portable device is disconnected from said client device in said client-server system;*
   sending said second information from said portable [proxy] device to said server device, *wherein (i) said second information is sent by said portable device to said client device in said client-server system when said portable device is connected to said client device, (ii) said second information is sent by said client device to said server device in said client-server system when said client device is connected to said server device, and (iii) said second information is stored in said server device;* [and]
   [comparing] *based on said second information, evaluating, in said server device, an effectiveness of* said [first information with said second information] *treatment regimen toward achieving treatment objectives or compliance with said treatment regimen; and*
   *automatically updating said treatment regimen in said server device to increase said effectiveness or said compliance, wherein (i) in a first mode, third information about the updated treatment regimen is sent by said server device to said client device in said client-server system and (ii) in a second mode, said second information and the updated treatment regimen are sent from said server device to a medical professional device that is separate from said server device so that a medical professional can review the updated treatment regimen and either leave the updated treatment regimen unchanged or modify the updated treatment regimen, and based upon the action taken by the medical professional sending said third information about the reviewed updated treatment regimen, taking into account the review of the medical professional, from said server device to said client device.*

2. A method as in claim 1, including steps for altering a sequence of processing steps at said portable [proxy] device in response to said *first* information received from said server device.

3. A method as in claim 1, including steps for altering a sequence of processing steps at said portable [proxy] device in response to a result of said steps for [comparing] *evaluating said effectiveness of said treatment regimen toward achieving treatment objectives or said compliance with said treatment regimen.*

4. A method as in claim 1, including steps for controlling a medicine dispenser coupled to said portable [proxy] device in response to said second information.

5. A method as in claim 1, including steps for presenting a reminder at said portable [proxy] device regarding following said treatment regimen *while said portable device is disconnected from said client device in said client-server system.*

6. A method as in claim [1] *5*, including steps for [presenting a] *receiving acknowledgement of the* reminder [from] *at* said [server] *portable* device [regarding compliance with said treatment regimen] *via said feedback input element while said portable device is disconnected from said client device in said client-server system.*

7. A method as in claim 1, including steps for presenting a result of said steps for [comparing] *evaluating the effectiveness of said treatment regimen toward achieving treatment objectives or said compliance with said treatment regimen* to [an operator at] said [server] *medical professional* device *via a communication network.*

8. A method as in claim 1, including steps for receiving [third] *and storing fourth* information [at] *from said patient via said feedback input element of* said portable [proxy] device *regarding an effect of an act performed responsive to said treatment regimen while said portable device is disconnected from said client device in said client-server system.*

9. A method as in cliam 8, where said [third] *fourth* information relates to an effect of medicine taken by said patient responsive to said reminder.

10. A method as in claim 8, including steps for altering said first information in response to said [third] *fourth* information.

* * * * *